(12) United States Patent
Zhou et al.

(10) Patent No.: US 10,905,461 B2
(45) Date of Patent: Feb. 2, 2021

(54) INTRODUCER SHEATH AND INTRODUCER

(71) Applicant: TERUMO KABUSHIKI KAISHA, Tokyo (JP)

(72) Inventors: Tuo Zhou, Kanagawa (JP); Ryo Okamura, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 218 days.

(21) Appl. No.: 16/038,534

(22) Filed: Jul. 18, 2018

(65) Prior Publication Data

US 2019/0021763 A1    Jan. 24, 2019

(30) Foreign Application Priority Data

Jul. 20, 2017    (JP) ................................. 2017-141307

(51) Int. Cl.
| | |
|---|---|
| *A61B 17/34* | (2006.01) |
| *A61M 25/06* | (2006.01) |
| *A61M 29/00* | (2006.01) |
| *A61M 25/00* | (2006.01) |

(52) U.S. Cl.
CPC ...... *A61B 17/3417* (2013.01); *A61B 17/3415* (2013.01); *A61M 25/0662* (2013.01); *A61B 2017/3433* (2013.01); *A61B 2017/3454* (2013.01); *A61M 29/00* (2013.01); *A61M 2025/0098* (2013.01)

(58) Field of Classification Search
CPC ...... A61M 2025/0098; A61M 25/0662; A61M 29/00; A61M 2025/0687; A61M 25/0141; A61B 17/3417; A61B 17/3415; A61B 2017/3433; A61B 2017/3454
See application file for complete search history.

(56) References Cited

U.S. PATENT DOCUMENTS

| | | | | |
|---|---|---|---|---|
| 6,053,904 | A  * | 4/2000 | Scribner | A61M 25/0017 |
| | | | | 604/104 |
| 6,120,480 | A  * | 9/2000 | Zhang | A61M 25/0662 |
| | | | | 604/164.01 |
| 6,808,509 | B1 * | 10/2004 | Davey | A61M 39/0606 |
| | | | | 604/164.05 |
| 10,400,068 | B2 * | 9/2019 | Kato | A61M 25/00 |
| | | | | 528/310 |
| 2016/0058976 | A1 * | 3/2016 | Okamura | A61M 25/0021 |
| | | | | 604/164.1 |
| 2017/0106168 | A1 * | 4/2017 | Sosnowski | A61B 17/1214 |

FOREIGN PATENT DOCUMENTS

| | | | | |
|---|---|---|---|---|
| WO | WO-2007145324 | A1 * | 12/2007 | ............. B32B 27/08 |
| WO | WO 2014/119527 | A1 | 8/2014 | |

* cited by examiner

*Primary Examiner* — Bhisma Mehta
*Assistant Examiner* — John J Crawford
(74) *Attorney, Agent, or Firm* — Buchanan Ingersoll & Rooney PC (57) ABSTRACT

An introducer sheath includes a tubular body configured to be percutaneously inserted into a body lumen and a hub that is connected to a proximal portion of the tubular body, wherein the tubular body contains a polyamide resin having a structural unit derived from a cyclic aliphatic hydrocarbon, and a wall thickness/inner diameter ratio of the tubular body is 1/14 or less, and a kink radius/outer diameter ratio of the tubular body is less than 10.

19 Claims, 6 Drawing Sheets

INTRODUCER SHEATH AND INTRODUCER

CROSS-REFERENCE TO RELATED APPLICATION

This application claims priority to Japanese Patent Application No. 2017-141307, filed on Jul. 20, 2017, the entire content of which is incorporated herein by reference.

TECHNICAL FIELD

The present invention relates to an introducer sheath for a medical instrument, such as an introducer, and an introducer including the introducer sheath and a dilator.

BACKGROUND ART

For introducing a catheter and the like into a body lumen, a medical instrument called an introducer has been used in the related art. The introducer is generally configured to have an introducer sheath having a hollow tubular body called a sheath tube and a hub provided on the tubular body, and a dilator assembled onto the introducer sheath.

The tubular body of the introducer sheath is percutaneously introduced into the body lumen (for example, a blood vessel) from a distal side. A hollow portion (lumen) formed in the inside of the tubular body is used as an access route that connects the inside and the outside of the living body. In use of such an introducer sheath, it is preferable that the tubular body has a large inner diameter and a small outer diameter, that is, a wall thickness that is as thin as possible. The tubular body formed to have a large inner diameter defines a large cross-sectional area of the hollow portion, and therefore an instrument such as a catheter can be smoothly introduced through the hollow portion, making the tubular body also possible to correspond with an instrument such as a catheter with a larger outer diameter. Meanwhile, the tubular body formed to have a small outer diameter makes insertion resistance to a body lumen small, leading to enhancement in insertion properties into the body lumen, and a puncture hole of a puncture site becomes small, and therefore it is possible to realize minimally invasive procedures.

If the tubular body of the introducer sheath is formed to have a thin wall thickness to some extent, strength against bending of the tubular body is decreased, and kinking of the tubular body is likely to occur. In a procedure using the introducer, the distal side of the tubular body is indwelled in the puncture site, and the hub is exposed to the outside of the living body by an operator. For this reason, in a state where a proximal side of the tubular body is bent with respect to the distal side thereof, an instrument such as a catheter is introduced into a body lumen through the hub by the operator. Therefore, when introducing a medical instrument into a hollow portion of the tubular body, the tubular body is required to have kink resistance so that kinking does not occur in the proximal side of the tubular body during the operation of introducing the medical instrument into the hollow portion of the tubular body. For example, PCT International Publication No. WO 2014/119527 proposes an introducer sheath configured such that even if kinking occurs in the tubular body, when pressure applied to the tubular body from the outside is released, a kinked portion of the tubular body can return so as to have an inner diameter which is almost the same as an original inner diameter.

As described above, it is preferable that in the tubular body of the introducer sheath, an inner diameter is large, and a wall thickness is as thin as possible from the viewpoint of enhancing performance, but there is a problem that kink resistance deteriorates in accordance with a decrease in wall thickness.

For example, when the tubular body is formed with a rigid material in order to increase the kink resistance of the tubular body, the tubular body lacks in flexibility, leading to a deterioration in followability to a body lumen and an increase in burden on a patient. Meanwhile, when the tubular body is formed by using a flexible material, a deterioration in the kink resistance is caused, and therefore it is difficult to form the tubular body to have a large inner diameter and a thin wall thickness.

Accordingly, it is required to appropriately set the inner diameter and the wall thickness of the tubular body of the introducer sheath so as to have a desired kink resistance, while considering physical properties of a material forming the tubular body.

SUMMARY

The disclosure herein is directed to an introducer sheath including a tubular body formed such that an inner diameter is larger, a wall thickness is thinner, and a kink resistance is enhanced compared to those of a tubular body in the related art.

The introducer sheath according to the disclosure herein includes a tubular body that is percutaneously inserted into a body lumen; and a hub that is connected to a proximal portion of the tubular body. The tubular body contains a polyamide resin having a structural unit derived from a cyclic aliphatic hydrocarbon, and a wall thickness/inner diameter of the tubular body ratio is 1/14 or less, and a kink radius/outer diameter of the tubular body ratio is less than 10.

In the tubular body according to the disclosure herein, a ratio of wall thickness/inner diameter is smaller than that of the tubular body in the related art. Therefore, it is possible that the tubular body has a large inner diameter and thin wall thickness. In addition, the tubular body contains a polyamide resin having a structural unit derived from a cyclic aliphatic hydrocarbon and has a small ratio of kink radius/outer diameter. For this reason, the tubular body has enhanced kink resistance. Therefore, according to the disclosure herein, it is possible to provide the introducer sheath including the tubular body formed such that the inner diameter is larger, the wall thickness is thinner, and the kink resistance is enhanced compared to those of the tubular body in the related art.

BRIEF DESCRIPTION OF THE DRAWINGS

is a cross-sectional view of the tubular body for explaining the kinked portion formed in the tubular body.

DESCRIPTION OF THE EMBODIMENTS

Hereinafter, an introducer sheath 100 according to the exemplary embodiment will be described with reference to each drawing. Note that the following description does not limit the technical scope, or the meaning of the terms described in the claims. In addition, in some cases, dimensional ratios in the drawings are exaggerated and are different from the actual ratios for the convenience of description.

FIGS. 1 to 3(B) are views for explaining each portion of the introducer sheath 100, and FIGS. 4 to 7(B) are views for explaining examples.

Figure 2:
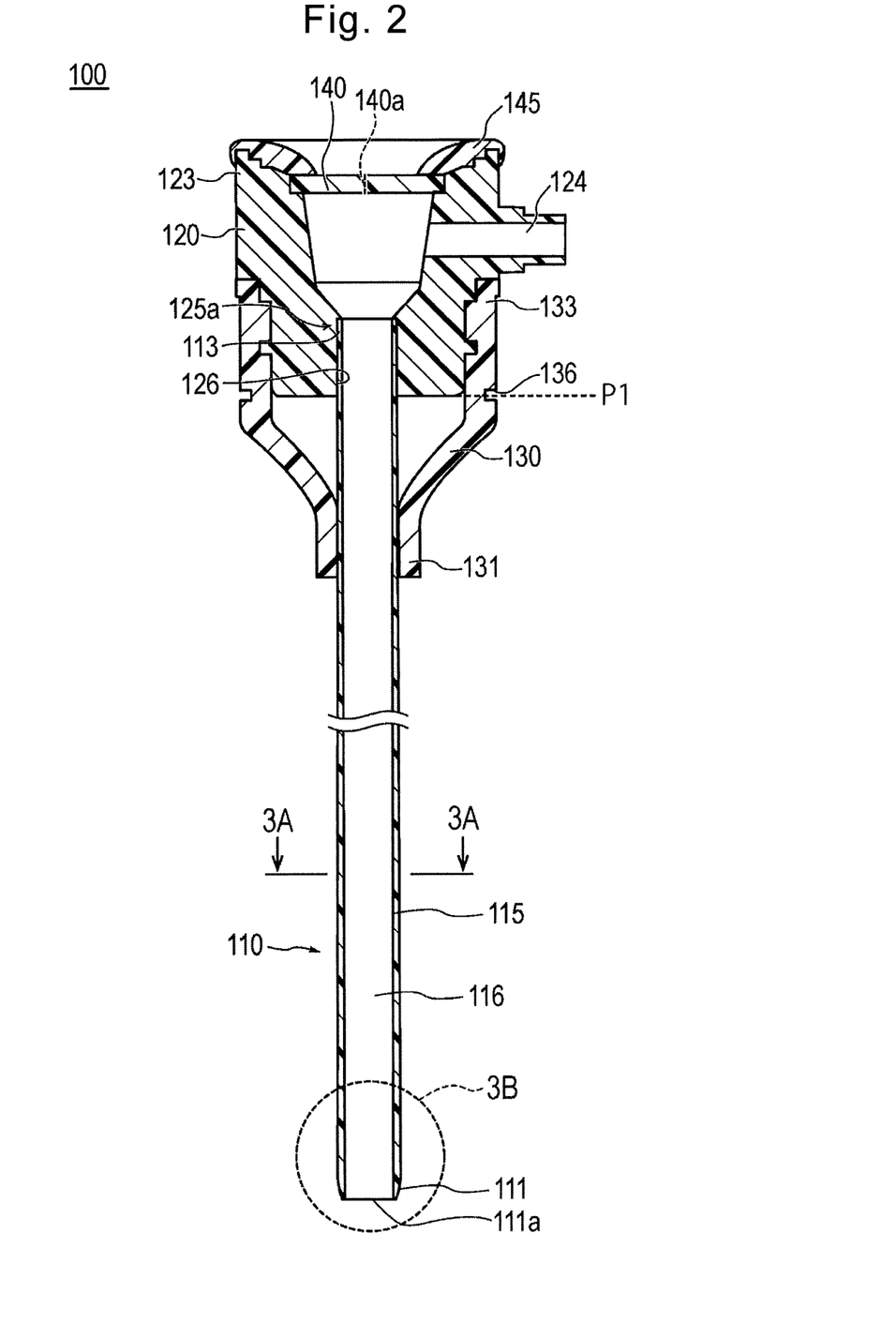
FIG. 2 is a cross-sectional view taken along an axial direction of an introducer sheath according to the exemplary embodiment.

With reference to FIG. 2, in the present specification, a side on which a hub (hub) 120 is disposed in the introducer sheath 100 (upper side in FIG. 2) will be referred to as "proximal side." A side positioned opposite to the proximal side in the introducer sheath 100 and which is to be introduced into a living body (lower side in FIG. 2) will be referred to as "distal side." In addition, a direction toward which the introducer sheath 100 is extended (vertical direction in FIG. 2) will be referred to as "axial direction" or "axis direction." In addition, the term "distal portion" in the explanation of the specification means a certain range including a distal end (most distal end) and the periphery thereof, and the term "proximal portion" means a certain range including a proximal end (most proximal end) and the periphery thereof.

Figure 1:
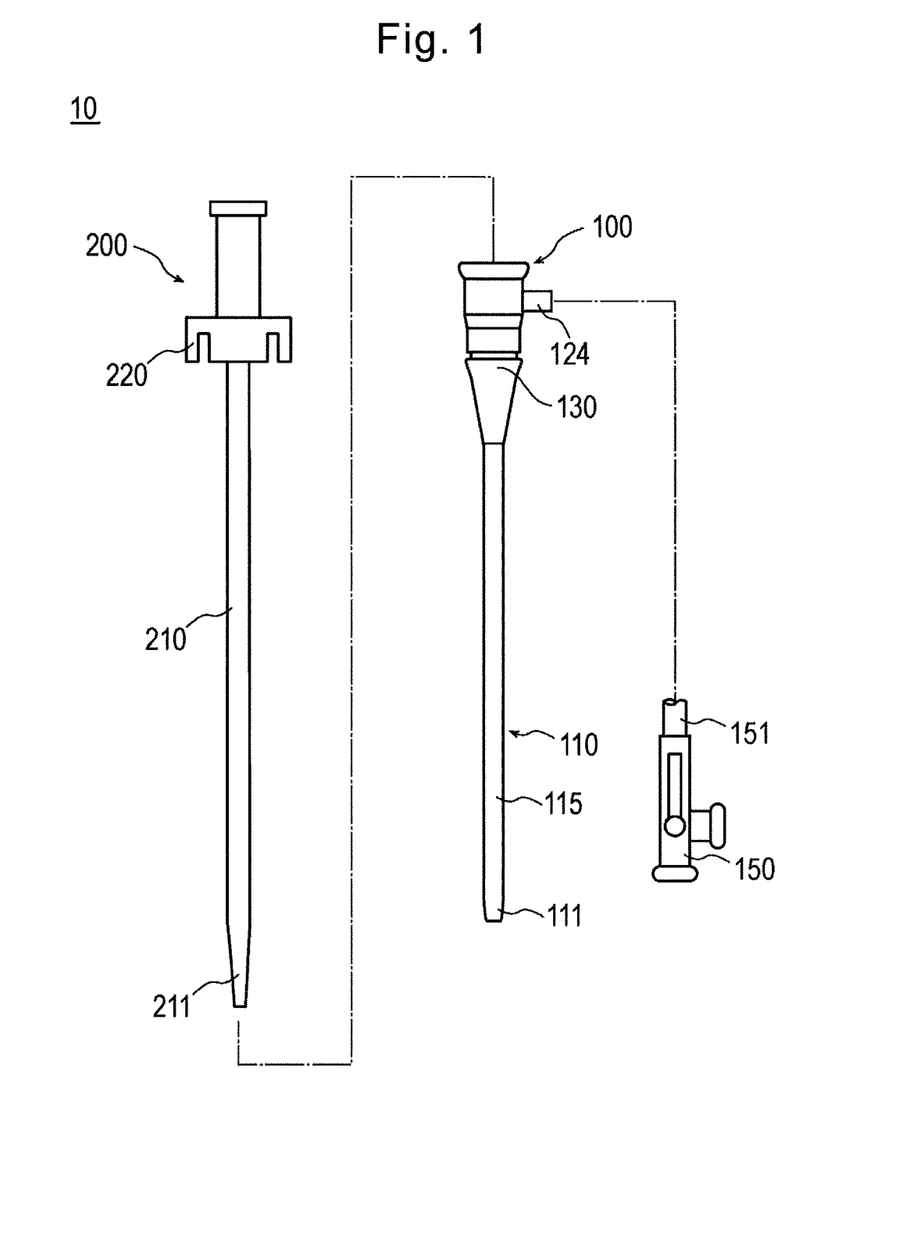
FIG. 1 is an exploded view illustrating an introducer according to an exemplary embodiment of the disclosure.

As shown in FIG. 1, an introducer 10 according to the present exemplary embodiment includes the introducer sheath 100 and a dilator 200.

The introducer sheath 100 is used, in a state where a distal side thereof is indwelled in a body lumen such as blood vessel and a proximal side thereof is exposed to the outside of a living body, such that instruments such as a catheter and a guide wire are inserted into the inside of the introducer sheath so as to be introduced into a body lumen.

As shown in FIG. 2, the introducer sheath 100 has a tubular body (sheath tube) 110 that has a hollow portion (lumen) 116 extending in an axial direction; a hub (sheath hub) 120 that is connected to a proximal side of the tubular body 110; and a strain relief portion 130 that is supported by a distal side of the hub 120 and covers a proximal portion 113 of the tubular body 110.

The tubular body 110 is formed of a tubular member having a substantially cylindrical shape. As shown in FIG. 2, the tubular body 110 has a tapered tubular distal portion 111; a tubular main body portion 115 that is disposed on a proximal side of the tubular distal portion 111; and a tubular proximal portion 113 that is disposed on a proximal side of the tubular main body portion 115 and interlocked by the hub 120. A distal end opening portion 111a is formed on a distal end of the tubular distal portion 111.

Figure 3A:
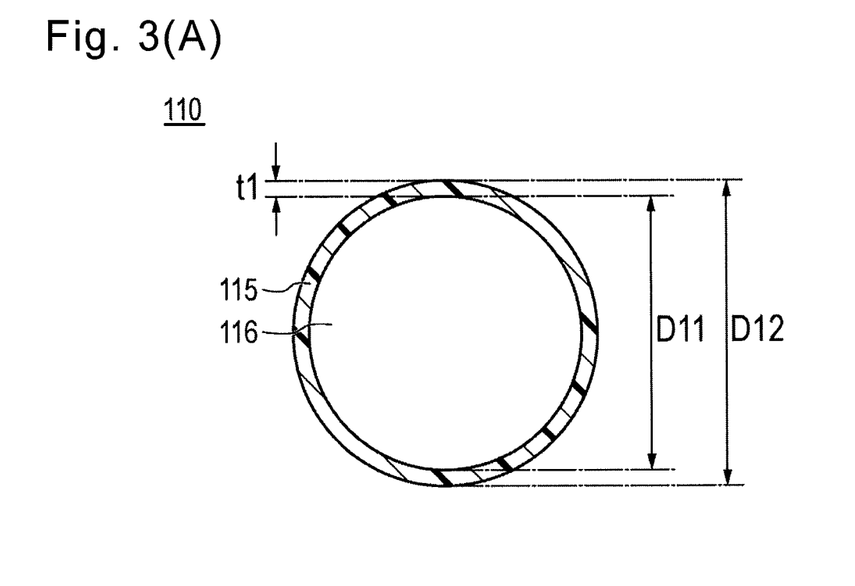
FIG. 3(A) is a cross-sectional view taken along line 3A-3A of FIG. 2.
Figure 3B:
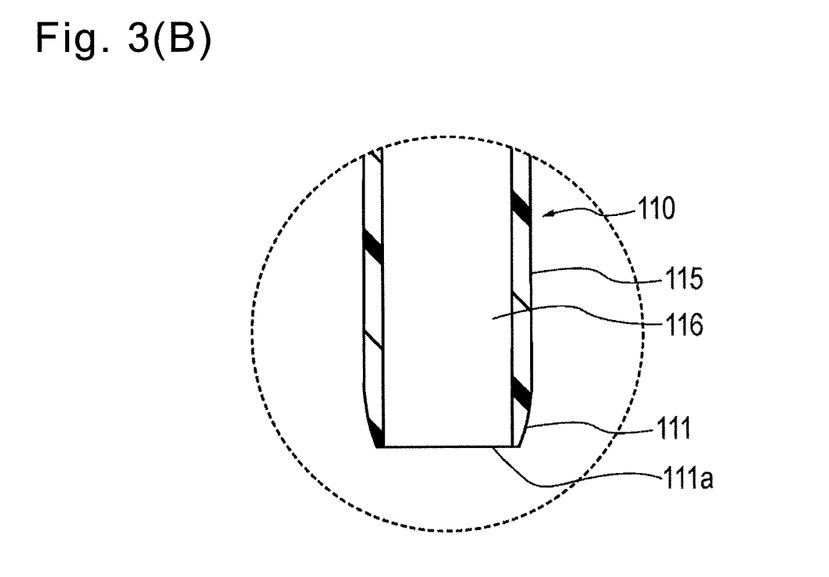
FIG. 3(B) is an enlarged view of a broken line portion 3B shown in FIG. 2.

FIG. 3(A) is a cross-sectional view (axially orthogonal cross-sectional view) of the tubular main body portion 115, which is taken along line 3A-3A of FIG. 2. In addition, FIG. 3(B) is an enlarged view of a broken line portion 3B of FIG. 2.

The tubular main body portion 115 of the tubular body 110 is defined by the dimensions (inner diameter D11, outer diameter D12, wall thickness t1) shown in FIG. 3(A), which are substantially constant along the axial direction. Meanwhile, as shown in FIG. 3(B), the tubular distal portion 111 of the tubular body 110 has a tapered shape in which an inner diameter is constant and an outer diameter tapers toward the distal side. The tubular proximal portion 113 of the tubular body 110 is fixed to the hub 120 as described below.

Note that an example of dimensions of the tubular main body portion 115 to be described below is an example of dimensions in a state before fixing the tubular body 110 to the hub 120.

As shown in FIG. 2, the hub 120 is provided with a lumen 126 to which the proximal portion 113 of the tubular body 110 is fixed, and a side port 124 that communicates with the lumen 126.

One end of a flexible tube 151 is connected to the side port 124 in a liquid tight manner (refer to FIG. 1). For example, a three-way stopcock 150 is mounted on the other end of the tube 151. A liquid such as a saline solution can be injected into the inside of the hollow portion 116 of the tubular body 110 from a port of the three-way stopcock 150 through the tube 151. The tube 151 can be constituted by a known tube made of polyvinyl chloride, for example.

A constituent material of the hub 120 is not particularly limited, but a rigid material such as rigid resin is suitable. Specific examples of the rigid resin include polyolefins such as polyethylene and polypropylene, polyamide, polycarbonate, polystyrene, and the like.

A proximal portion 123 of the hub 120 is attached with a valve body 140 for preventing a liquid, such as blood flowing into the tubular body 110, from leaking to the outside. The valve body 140 is formed of an elastic member in which a slit 140a is formed that enables the insertion of a dilator main body 210. The valve body 140 is formed to have a substantially elliptical membrane shape (disk shape) and is fixed to the hub 120 in a liquid tight manner by a predetermined cap 145 being fitted to the valve body.

A constituent material of the valve body 140 is not particularly limited, but examples thereof include silicone rubber, latex rubber, butyl rubber, isoprene rubber, and the like which are elastic members.

The proximal portion 113 of the tubular body 110 is fixed to an interlock portion 125a of the hub 120. The proximal portion 113 of the tubular body 110 can be fixed to the interlock portion 125a of the hub 120 by an adhesive, for example.

As shown in FIG. 2, the strain relief portion 130 is externally fitted with respect to the tubular body 110 and the hub 120. A distal portion 131 of the strain relief portion 130 is disposed so as to cover a certain range of a proximal side of the tubular body 110. In addition, a proximal portion 133 of the strain relief portion 130 is disposed so as to cover a certain range of the distal side of the hub 120 and covers the interlock portion 125a to which the tubular body 110 and the hub 120 are interlocked.

The strain relief portion 130 has a concave portion 136 on a position overlapping with a distal end P1 of the hub 120 in the axial direction. Note that the distal end P1 of the hub 120 can be used as a reference for determining a press position of the tubular body 110 when carrying out a measurement test on a kink generation angle which is to be described below (refer to FIG. 5).

A constituent material of the strain relief portion 130 is not particularly limited, but examples thereof include natural rubber, silicone resin, and the like.

As shown in FIG. 1, the dilator 200 has a dilator main body 210 that is insertable into the tubular body 110, and a dilator hub 220 configured to be connectable to the hub 120.

The dilator 200 is used for preventing breakage of the tubular body 110 or for enlarging a puncture hole of the skin when inserting the tubular body 110 of the introducer sheath 100 into a body lumen.

When the dilator main body 210 is inserted into the tubular body 110, a distal portion 211 thereof protrudes from the distal end opening portion 111a of the tubular body 110. The distal portion 211 of the dilator main body 210 is formed to have a tapered shape that tapers toward the distal side.

A constituent material of the dilator hub 220 is not particularly limited, but a rigid material such as rigid resin is suitable. Specific examples of the rigid resin include polyolefins such as polyethylene and polypropylene, polyamide, polycarbonate, polystyrene, and the like.

Next, the tubular body 110 and the dilator main body 210 will be described in detail.

The tubular body 110 is constituted by a polyamide resin having a structural unit derived from a cyclic aliphatic hydrocarbon (hereinafter, this will simply be referred to as "polyamide resin" in the disclosure). The polyamide resin contains a cyclic aliphatic hydrocarbon as a constitutional unit of a copolymer. By containing the cyclic aliphatic hydrocarbon as a constituent unit of the copolymer, a steric space is formed in the resin due to steric hindrance. Therefore, it is presumed that it is possible to suitably suppress the tubular body 110 from being deformed by external forces acted thereon from various directions. In a procedure using the introducer 10, an operator inserts a medical instrument into a body lumen through the hub 120 in a state where the operator inserts the distal side of the tubular body 110 into the body lumen and grips the hub 120 exposed outside the living body, and therefore the proximal side of the tubular body 110 becomes bent with respect to the distal side. The tubular body 110 according to the exemplary embodiment of the disclosure can be suppressed from being deformed by external forces acted thereon from various directions as described above, and therefore when the proximal side of the tubular body 110 becomes bent with respect to the distal side, it is possible to suitably prevent kinking from occurring. Accordingly, the operator can smoothly introduce a medical instrument into the hollow portion 116 of the tubular body 110. Note that as used in the disclosure herein, the term "kinking" means that "after the tubular body 110 is applied with external force and thus the tubular body is bent, even when the external force is released, the tubular body 110 does not return to an original shape, resulting in bending behavior (the tubular body 110 is plastically deformed due to bending)."

The polyamide resin has, for example, a structural unit (A) derived from a crystallin linear aliphatic dicarboxylic acid and a structural unit (B) derived from an amorphous alicyclic diamine. For this reason, the polyamide resin has both crystalline and amorphous characteristics (characteristics as microcrystals). Therefore, the tubular body 110 has high flexibility compared to a case in which a crystalline resin is used as a material for forming the tubular body, and has high rigidity compared to a case in which an amorphous resin is used as a material for forming the tubular body. As described above, since the tubular body 110 has appropriate flexibility and rigidity, it is possible to suitably maintain followability to a shape of a body lumen, and it is possible to suitably suppress the occurrence of kinking and deflection and turnover of the tubular body 110 which occur when inserting the introducer 10 into the body lumen. Furthermore, in a state where the distal side of the tubular body 110 is indwelled in the body lumen and the hub 120 is exposed outside the living body, the tubular body 110 is tightened or squeezed in a radial direction (in a direction toward a center of the lumen of the tubular body 110) by biological tissues around a puncture site. In particular, when inserting the introducer sheath 100 into a blood vessel in a part of which a thickness of limbs such as a lower limb is thick, a pressing force by which the tubular body 110 is tightened in the radial direction by biological tissues around the puncture site, becomes large. The tubular body 110 has an appropriate rigidity as described above, and therefore the tubular body 110 is suppressed from being squashed against the pressing force from the tightening in the radial direction. That is, when the introducer 10 is indwelled in a body lumen, the tubular body 110 can maintain an inner surface thereof in a shape close to a perfect circle in an axially orthogonal cross section. Therefore, the operator can smoothly introduce a medical instrument into the hollow portion 116 of the tubular body 110. Because the deformation of the tubular body 110 which occurs by the tubular body 110 being tightened in the radial direction by biological tissues around the puncture site is generally an elastic deformation, the tubular body 110 returns to its original shape when the pressing force is released (a state where the introducer sheath 100 is withdrawn to the outside of a living body). As described above, it is preferable that the tubular body 110 suitably maintains not only the kink resistance (difficulty in plastic deformation) but also retention properties (difficulty in elastic deformation) of the hollow portion 116.

Specific examples of the structural unit (A) derived from a linear aliphatic dicarboxylic acid include the following structure.

In Formula (1), $R_1$ represents an alkylene group having 8 or more carbon atoms, preferably represents an alkylene group having 8 to 20 carbon atoms, and more preferably represents an alkylene group having 8 to 12 carbon atoms.

Specific examples of the structural unit (B) derived from an alicyclic diamine include the following structure.

In Formula (2), $R_2$ represents an alkylene group having 2 or 3 carbon atoms, preferably 2 carbon atoms, and $R_3$ and $R_4$ each independently represent a hydrogen atom or a methyl group.

A compositional ratio of the structural unit (A) and the structural unit (B) is not particularly limited, but it is preferable that the constitutional unit (B) is 1 to 49 mol % with respect to a total 100 mol % of the structural unit (A) and the structural unit (B).

Such a copolymer can be obtained by, for example, copolymerizing an aliphatic dicarboxylic acid having 8 or more carbon atoms and an alicyclic diamine. Examples of the aliphatic dicarboxylic acid having 8 or more carbon atoms include suberic acid, azelaic acid, sebacic acid, undecanedioic acid, dodecanedioic acid, tetradecanedioic acid, hexadecanedioic acid, and the like. Among these, dodecanedioic acid is particularly preferable. Specific examples of the alicyclic diamine include 4,4'-methylenebis(cyclohexylamine), 4,4'-methylenebis(1-amino-2-methylcyclohexane), 2,2-bis(4-aminocyclohexyl)propane, and the like. Among these, 4,4'-methylenebis(cyclohexylamine) is particularly preferable. Note that when the copolymerization is carried out, other diamines may be contained. In addition, the polycondensation of the alicyclic diamine and the aliphatic dicarboxylic acid can be carried out by using a method which is generally performed in the related art.

A coating layer having lubricity can be formed on an outer surface and/or the inner surface of the tubular body 110. As a material for forming the coating layer, it is possible to use a known coating material of the related art which is hydrophilic or hydrophobic. The exemplary dimensions described below refer to the dimensions of the tubular body 110 itself, which do not include the size (thickness) of the coating layer even when the coating layer is formed on the tubular body 110.

Referring to FIG. 3(A), in the tubular body 110, a ratio of the wall thickness t1 to the inner diameter D11 of the tubular main body portion 115 (expressed as: wall thickness t1/inner diameter D11) is 1/14 or less. The wall thickness t1/inner diameter D11 of the tubular main body portion 115 is preferably 1/22.2 to 1/14.8.

Each dimension of the tubular main body portion 115 is not particularly limited as long as the wall thickness t1/inner diameter D11 ratio of the tubular main body portion 115 is 1/14 or less, but the tubular main body portion 115 can be formed with the following dimensions, for example.

The tubular main body portion 115 can be formed to have the inner diameter D11 of 1.9 mm to 2.5 mm. In this case, preferably, the wall thickness t1 is 0.050 to 0.150 mm and the outer diameter D12 is 2.0 mm to 2.80 mm. Within these exemplary ranges for the wall thickness t1 and the inner diameter D11, a value for each is chosen so as to meet the preferred ratio that the wall thickness t1/inner diameter D11 is 1/14 or less. By way of example, a wall thickness t1 of 0.150 mm can be used with an inner diameter D11 of 1.9 mm to provide a ratio of 1/12.6. In addition, the tubular main body portion 115 can be formed to have the inner diameter D11 of 1.1 mm to 2.0 mm. In this case, preferably, the wall thickness t1 is 0.050 to 0.120 mm and the outer diameter D12 is 1.2 mm to 2.24 mm.

In the exemplary embodiment, the ratio of the kink radius Rk to the outer diameter D12 of the tubular main body portion 115 (expressed as: kink radius Rk/the outer diameter D12) is 10 or less. The kink radius Rk/outer diameter D12 of the tubular main body portion 115 is preferably 8.3 or less. The kink resistance of the tubular main body portion 115 generally depends on the wall thickness t1, that is, a size of the outer diameter D12 when it is assumed that the inner diameter D11 is constant, and therefore as the outer diameter D12 becomes large, the kink resistance is enhanced. In other words, the kink resistance depends on the outer diameter D12 (wall thickness). In the tubular main body portion 115 of the exemplary embodiment, the kink radius Rk/outer diameter D12 is 10 or less, which is a comparatively small value, and therefore it is considered that the kink resistance is enhanced while considering dependency on the outer diameter D12 (wall thickness). Note that a method for measuring the kink radius Rk will be described below.

Figure 5:
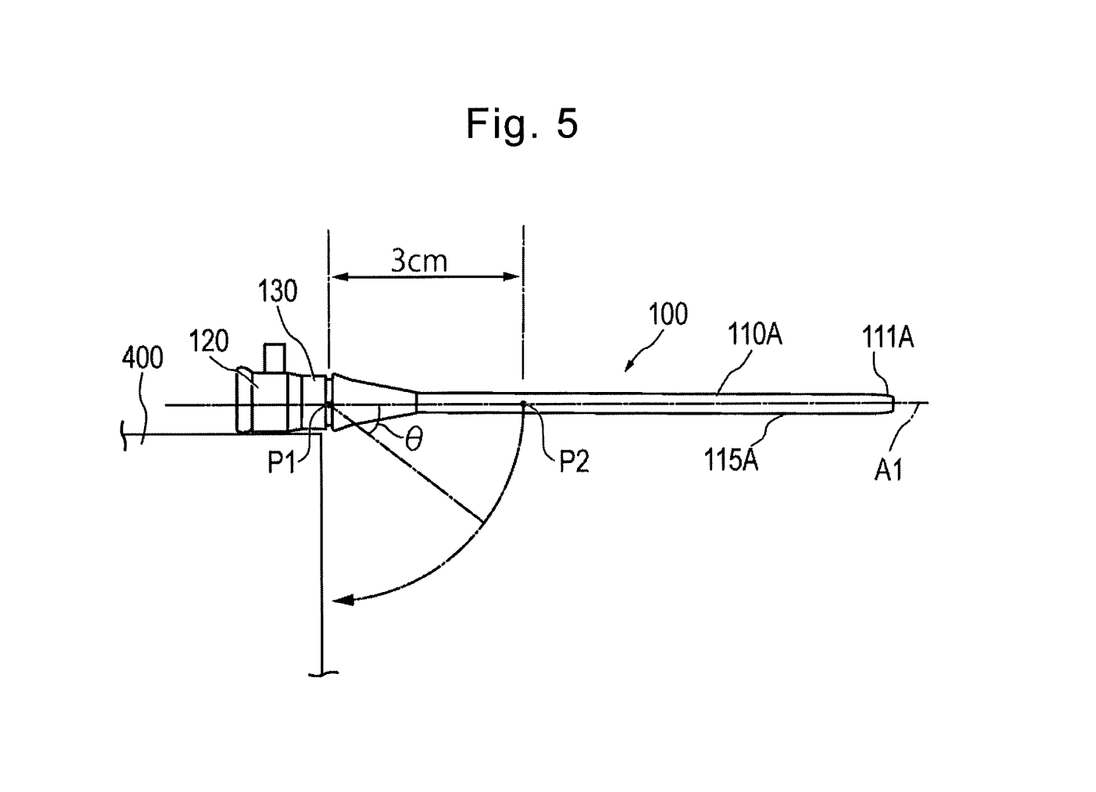
FIG. 5 is a schematic view showing a method for measuring a kink generation angle.

In addition, in the exemplary embodiment, a kink generation angle θ occurs when a position P2, at 3 cm away from the distal end P1 of the hub 120, is pressed 32° or greater, in a state where the proximal side of the introducer sheath 100 is held and fixed at a support 400 (refer to FIG. 5). Therefore, when the operator performs various operations in a state where the distal side of the tubular body 110 is indwelled into a body lumen and the proximal side of the tubular body 110 is bent with respect to the distal side, the tubular body 110 can suitably prevent the kinking from occurring in the proximal side thereof. Note that a method for measuring the kink generation angle θ will be described below.

Figure 7A:
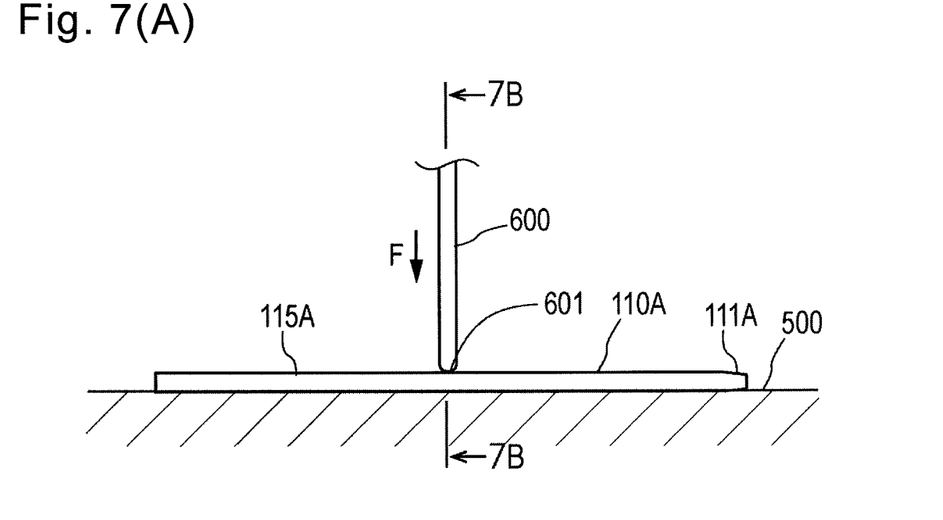
FIG. 7(A) is a schematic view showing a method for measuring a roundness rate of the tubular body in a state where the tubular body is pressed by a constant load.
Figure 7B:
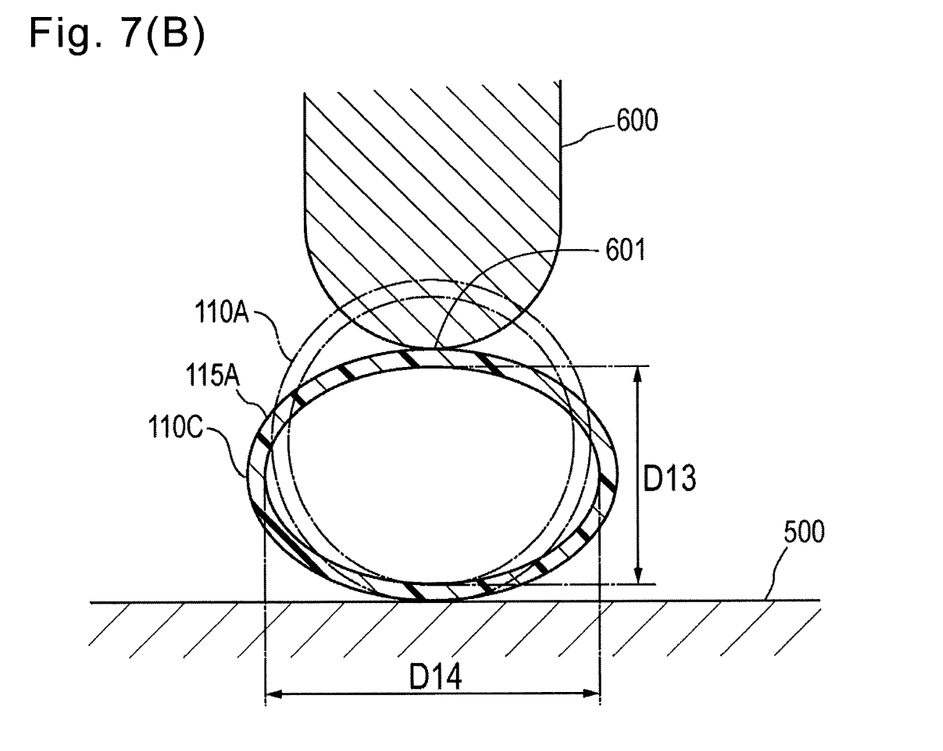
FIG. 7(B) is a cross-sectional view taken along line 7A-7A of FIG. 7(A).

In the exemplary embodiment, when a solid rod member 600 with an outer diameter of 2 mm is pushed against the tubular body 110 with a force F of 150 gf in a direction perpendicular to the tubular body 110, a lumen retention rate of a position where the rod member 600 is pushed against the tubular body 110 is 6.3 or greater, the lumen retention rate being defined as a roundness rate of the inner surface/wall thickness t1 of the tubular body 110 (refer to FIG. 7(B)). The lumen retention rate of the tubular main body portion 115 is preferably 0.62 or greater. Therefore, the tubular body 110 can be suppressed from being squashed in the radial direction when the tubular body 110 is tightened in the radial direction by biological tissues around the puncture site. That is, the tubular body 110 can maintain the inner surface thereof in a shape close to a perfect circle, i.e., substantially circular, in the axially orthogonal cross section passing through the position of the tubular body 110 against which the solid rod member 600 is pushed. Accordingly, the operator can smoothly introduce a medical instrument into the hollow portion 116 of the tubular body 110. Note that a method for measuring the roundness rate and the lumen retention rate will be described below.

In the exemplary embodiment, the dilator main body 210 has flexural rigidity higher than that of the tubular body 110. A method for increasing a flexural rigidity rate of the dilator main body 210 to be higher than flexural rigidity of the tubular body 110 is not particularly limited, but for example, a method in which a wall thickness of the dilator main body 210 is made to be thicker than the wall thickness of the tubular body 110, a method in which the dilator main body 210 is made of a material having a bending modulus of elasticity (ISO 178 JIS K 7171) higher than that of a constituent material of the tubular body 110, and the like can be used.

In the exemplary embodiment of the disclosure, the tubular body 110 and the dilator main body 210 are constituted by hollow members. For this reason, by making the wall thickness of the dilator main body 210 thicker than the wall thickness of the tubular body 110, the flexural rigidity of the dilator main body 210 is made to be higher than the flexural rigidity of the tubular body 110. Therefore, when the tubular body 110 is inserted into a body lumen in a state where the dilator main body 210 is inserted in the hollow portion 116 of the tubular body 110 to form the introducer 10, a strong elastic force is applied to the tubular body 110 due to the dilator main body 210. Accordingly, turnover and kinking can be prevented from occurring in the tubular body 110.

Examples of the material constituting the dilator main body 210 include polyolefins such as polypropylene (PP) and polyethylene (PE), polyesters such as nylon and polyethylene terephthalate (PET), fluorine-based polymers such as polyvinylidene fluoride (PVDF) and tetrafluoroethylene-hexafluoropropylene copolymer (FEP), and the like.

In addition, in the exemplary embodiment disclosed herein, in the tubular body 110, the tubular distal portion 111 is configured to be more rigid than the tubular main body portion 115. The tubular distal portion 111 is formed to have the tapered shape in which the outer diameter thereof is gradually decreased toward the distal side, and therefore turnover is likely to occur in the tubular distal portion 111 when the tubular body 110 is inserted into a body lumen. In addition, the tubular distal portion 111 is formed to have the tapered shape, and therefore the kink resistance deteriorates compared to that of the tubular main body portion 115. Accordingly, in the exemplary embodiment, by forming the tubular distal portion 111 more rigid than the tubular main body portion 115, turnover is prevented from occurring in the tubular distal portion 111 when the tubular body 110 is inserted into a body lumen. Based on the above configuration, the tubular distal portion 111 also has enhanced kink resistance.

Next, embodiments of the disclosure herein will be more specifically described based on examples, but the disclosure is not limited to the following examples.

Measurement Test of Kink Radius

The kink radius Rk of tubular bodies of Examples 1 to 3 and a tubular body of Comparative Example 1 (hereinafter, tubular bodies of each example and comparative example will be collectively referred to as "tubular body 110A") was measured. Note that in the drawing, a distal portion of the tubular body 110A is denoted as a reference numeral 111A, and a tubular main body portion is denoted as a reference numeral 115A (refer to FIGS. 4 to 7(B)).

Test Sample (1) Tubular body of Example 1: formed of a resin obtained by polymerizing dodecanedioic acid and 4,4'-methylenebis(cyclohexylamine), wall thickness t1=0.10 mm, inner diameter D11=2.22 mm, outer diameter D12=2.42 mm.

(2) Tubular body of Example 2: formed of a resin obtained by polymerizing dodecanedioic acid and 4,4'-methylenebis(cyclohexylamine), wall thickness t1=0.12 mm, inner diameter D11=2.22 mm, outer diameter D12=2.46 mm.

(3) Tubular body of Example 3: formed of a resin obtained by polymerizing dodecanedioic acid and 4,4'-methylenebis(cyclohexylamine), wall thickness t1=0.15 mm, inner diameter D11=2.22 mm, outer diameter D12=2.52 mm.

(4) Tubular body of Comparative Example 1: formed of an ethylene tetrafluoroethylene (ETFE) resin, wall thickness t1=0.12 mm, inner diameter D11=2.22 mm, outer diameter D12=2.46 mm.

Test Method and Evaluation Method

Figure 4:
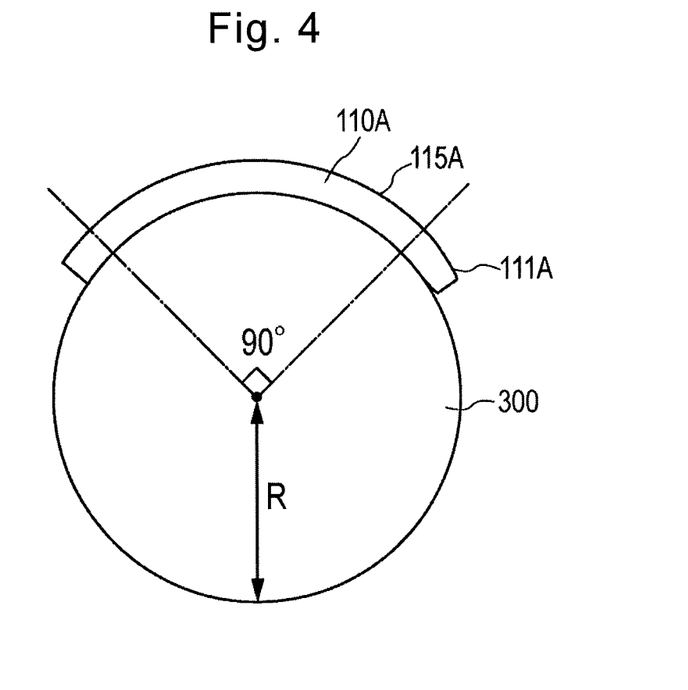
FIG. 4 is a schematic view showing a method for measuring a kink radius.
Figure 6A:
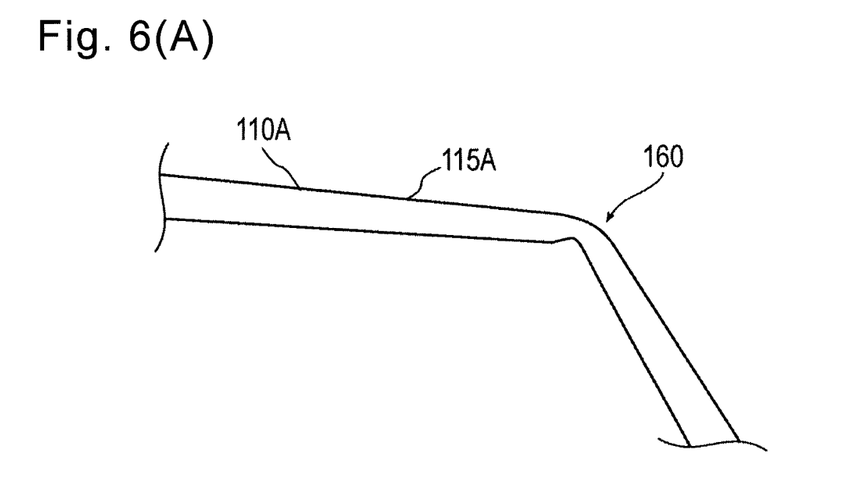
FIG. 6(A) is a side view of a tubular body for explaining a kinked portion formed in the tubular body, and FIG. 6(B)
Figure 6B:
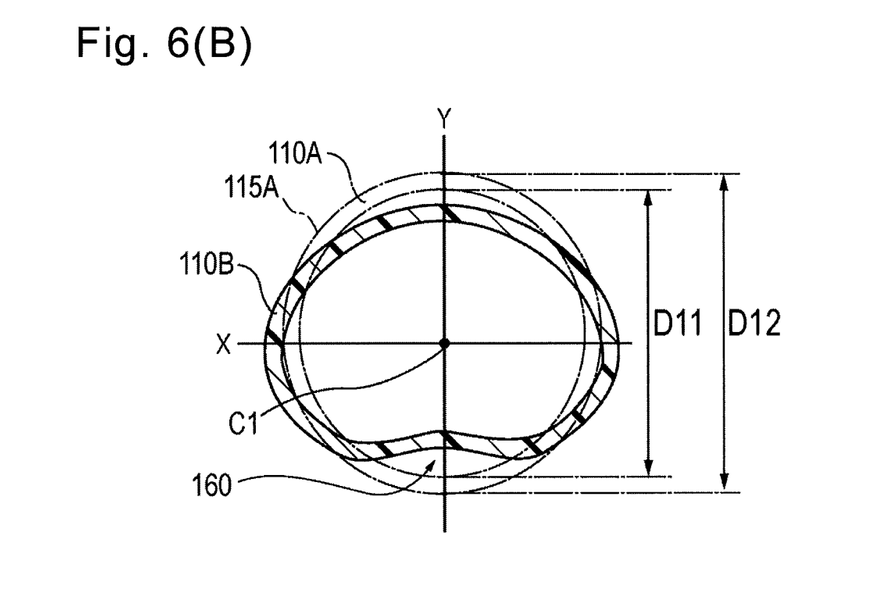

In the measurement test of the kink radius Rk, a test instrument 300 made of a circular member shown in FIG. 4 was used. The presence or absence of kinking of the tubular body 110A was checked when the test instrument 300 having a radius R of 150 mm to 5 mm is used, the tubular body 110A is placed along the test instrument 300, and the tubular body 110A is bent by 90° with respect to a center of the test instrument 300. The test was carried out five times for each example and comparative example. Table 1 shows the test results. Note that the kink radius Rk shown in Table 1 is a radius of curvature when the kinking occurred in each example and comparative example. That is, the kink radius Rk is a radius R of the test instrument 300 used when the kinking occurs in the tubular body 110A. Note that, as shown in FIG. 6(A), the presence or absence of the kinking occurrence was determined based on whether or not a kinked portion 160 was formed in the tubular body 110A. As shown in FIG. 6(B), a tubular body 110B after the kinking occurrence develops a flat shape in an X-axis direction or a Y-axis direction passing through a center C1 of the tubular body 110B in the axially orthogonal cross section, compared to the tubular body 110A before the kinking occurrence. As a result of the measurement test, when it was checked that the tubular body 110A was deformed into the flat shape, it was assumed that the kinking occurred in the tubular body 110A. The cross-sectional shape when the kinking occurred as shown in FIG. 6(B) is an example of when a shape became flat (squashed shape) compared to a shape before the kinking occurrence, it was assumed that the kinking occurred in the tubular body 110A.

TABLE 1

| | Kink radius Rk (mm) | | | |
|---|---|---|---|---|
| | Example 1 (t1 = 0.10) | Example 2 (t1 = 0.12) | Example 3 (t1 = 0.15) | Comparative Example 1 (t1 = 0.12) |
| Test 1 | 20 | 15 | 13 | 25 |
| Test 2 | 20 | 15 | 13 | 25 |
| Test 3 | 20 | 15 | 15 | 30 |
| Test 4 | 20 | 15 | 13 | 25 |
| Test 5 | 20 | 15 | 14 | 25 |
| Maximum value | 20 | 15 | 15 | 30 |
| Minimum value | 20 | 15 | 13 | 25 |
| Outer diameter of tubular body (mm) | 2.42 | 2.46 | 2.52 | 2.46 |
| Maximum kink radius Rk/outer diameter of tubular body | 8.3 | 6.1 | 6.1 | 10.2 |
| Minimum kink radius Rk/outer diameter of tubular body | 8.3 | 6.1 | 5.2 | 12.2 |

Evaluation Result

As can be seen from Table 1, when comparing Example 2 in which the wall thickness was formed to be 0.12 mm and Comparative Example 1 in which the wall thickness was formed to be 0.12 mm, it was found that both values of a minimum value and a maximum value of the kink radius Rk of the tests carried out 5 times were smaller in Example 2 compared to those of the comparative example, that is, the kink resistance was higher. Based on the results, it was found that in the case in which the resin obtained by polymerizing dodecanedioic acid and 4,4'-methylenebis(cyclohexylamine) was used as the material forming the tubular body 110A, the kink resistance of the tubular body 110A was enhanced compared to the case in which the ethylene tetrafluoroethylene resin was used.

In addition, any one of maximum values of the kink radius Rk of Example 1 to 3 was smaller than the minimum value of the kink radius Rk of Comparative Example 1. Based on the results, it was found that in the case in which the resin obtained by polymerizing dodecanedioic acid and 4,4'-methylenebis(cyclohexylamine) was used as the material forming the tubular body 110A, there was the tendency that the kink resistance of the tubular body 110A was generally enhanced.

In addition, when comparing Example 2 and Example 3, it was found that the kink resistance of both examples was the same as each other, in spite of the thinner wall thickness of Example 2. Based on the results, it was found that by using the resin obtained by polymerizing dodecanedioic acid and 4,4'-methylenebis(cyclohexylamine) as the material forming the tubular body 110A, the effect on the kink resistance due to the thinness of the wall thickness was reduced. Therefore, it was found that by using the resin obtained by polymerizing dodecanedioic acid and 4,4'-methylenebis(cyclohexylamine) so as to form the tubular body 110A, it is possible to secure the desired kink resistance even when the wall thickness of the tubular body 110A is formed to be thin.

From Table 1, it is apparent that all of the minimum value of the kink radius Rk/outer diameter ratios in Examples 1 to 3 were 10 or less. Therefore, it was found that when the resin obtained by polymerizing dodecanedioic acid and 4,4'-methylenebis(cyclohexylamine) was used as the material forming the tubular body 110A, if the ratio of the minimum value of the kink radius Rk/outer diameter was 10 or less, it is possible to obtain favorable kink resistance in which the minimum value of the kink radius Rk in the tubular bodies 110A of Examples 1 to 3 becomes about 13 to 20 mm.

In a procedure in which the introducer sheath 100 is indwelled in the radial artery and an instrument such as a catheter is introduced into the brachial artery or the aorta, a puncture angle is generally about 30°, and the tubular body 110 is bent to about a radius of curvature of 80 mm during the procedure. In addition, in a procedure in which the introducer sheath 100 is indwelled in the common femoral artery and the superficial femoral artery and an instrument such as a catheter is introduced into the aorta, it is considered that a puncture angle is generally about 45° to 60°, and the tubular body 110 is bent to about a radius of curvature of 30 to 60 mm during the procedure. In the case where the ratio of the minimum value of the kink radius Rk/outer diameter is set to be 10 or less so that the minimum value of the kink radius Rk becomes 13 to 20 mm, it is possible to prevent the kinking from occurring in the tubular body 110 at least in the above procedures.

Measurement Test of Kink Generation Angle

Test Sample

A kink generation angle of the introducer sheath 100 having the tubular bodies 110A of Examples 1 to 3 and Comparative Example 1, was measured. The introducer sheath 100 used in the test was configured to be the same as that of the above-described exemplary embodiment (refer to FIG. 2). Specifically, an introducer sheath in which the tubular bodies 110A of Examples 1 to 3 and Comparative Example 1 were respectively mounted with the hub 120 and the strain relief portion 130, was used as the introducer sheath 100.

Test Method and Evaluation Method

As shown in FIG. 5, in the measurement test of the kink generation angle, in a state where a part of the hub 120 and the strain relief portion 130 was fixed on the support 400, a position P2 which was 3 cm away from the distal end P1 of the hub 120 (refer to FIG. 2) was pressed with a finger so as to allow the tubular body 110A to bent downward until the kinking occurred in the tubular body 110A. When the kinking occurred in the tubular body 110A, a bending angle θ based on an axis center A1 of the tubular body 110A was measured, and the measurement result was taken as the kink generation angle. Note that the presence or absence of the kink occurrence was checked with the same criteria as the above-described measurement test of the kink radius Rk (refer to FIGS. 6(A)-7(B)). The test was carried out five times for the introducer sheath 100 including the tubular body 110A of each example and comparative example. The test results are shown in Table 2.

TABLE 2

| | Kink generation angle (°) | | | |
|---|---|---|---|---|
| | Example 1 (t1 = 0.10) | Example 2 (t1 = 0.12) | Example 3 (t1 = 0.15) | Comparative Example 1 (t1 = 0.12) |
| Test 1 | 35 | 40 | 46 | 30 |
| Test 2 | 33 | 41 | 45 | 29 |
| Test 3 | 36 | 40 | 52 | 26 |
| Test 4 | 35 | 39 | 47 | 28 |
| Test 5 | 33 | 41 | 53 | 31 |
| Average value | 34.4 | 40.2 | 48.6 | 28.8 |
| Maximum value | 36 | 41 | 53 | 31 |
| Minimum value | 33 | 39 | 45 | 26 |

Evaluation Result

From the test results shown in Table 2, it was found that among Examples 1 to 3, the smallest kink generation angle was 33° in Example 1. In addition, it was found that the largest kink generation angle was 53° in Example 3. In contrast, in Comparative Example 1, a minimum value of the kink generation angle was 26°. As described above, by using the resin obtained by polymerizing dodecanedioic acid and 4,4'-methylenebis(cyclohexylamine) as the material forming the tubular body 110A, it was possible to enhance the kink resistance of the tubular body 110A such that the kink generation angle became 33°, at the minimum.

Measurement Test of Lumen Retention Rate when Tubular Body is Pressed with Constant Load Test Sample In addition to the tubular bodies 110A of Examples 1 and 2 and the tubular body 110A of Comparative Example 1, with respect to tubular bodies 110A of Comparative Examples 2 and 3, a roundness rate and a lumen retention rate of the tubular body 110A when the tubular body 110A was pressed with a constant load were measured. The tubular bodies of Comparative Examples 2 and 3 were formed as follows.

(1) Tubular body of Comparative Example 2: formed of polyamide 12 (PA12) resin, wall thickness t1=0.10 mm, inner diameter D11=2.22 mm, outer diameter D12=2.42 mm.

(2) Tubular body of Comparative Example 3: formed of polyamide 12 (PA12) resin, wall thickness t1=0.12 mm, inner diameter D11=2.22 mm, outer diameter D12=2.46 mm.

Test Method and Evaluation Method

As shown in FIG. 7(A), in the measurement test of the lumen retention rate, the tubular body 110A was pressed with a constant load. A solid rod member 600 with an outer diameter of 2 mm, and which has a rounded distal end, was pushed against the tubular body 110A with a force F of 150 gf in a direction perpendicular to the tubular body 110A, in a state where the tubular body 110A was fixed to a support 500. As shown in FIG. 7(B), a position of the tubular body 110A against which the rod member 600 was pressed was squashed into a substantially elliptical shape (indicated by reference numeral 110C in the drawing). Silicone was injected into the hollow portion 116 of a squashed tubular body 110C while the rod member 600 was pressed against the tubular body 110C, and a mold of the hollow portion 116 was taken. Thereafter, a minor axis length and a major axis length of an outer shape (substantially elliptical shape) of the hollow portion 116 in the axially orthogonal cross section passing through the portion squashed by the rod member 600 were measured. That is, the minor axis length corresponds to a minor axis length D13 of an inner surface of the tubular body 110C in the axially orthogonal cross section passing through a position 601 of the tubular body 110A against which the rod member 600 was pressed, and the major axis length corresponds to a major axis length D14 of the inner surface of the tubular body 110C in the axially orthogonal cross section passing through the position 601 of the tubular body 110A against which the rod member 600 was pressed. A roundness rate (minor axis length D13/major axis length D14) and a lumen retention rate (roundness rate/wall thickness) were calculated from the measured minor axis length D13 and major axis length D14. The test was carried out five times for the tubular body 110A of each example and comparative example. The test results are shown in Tables 3 and 4. Note that in the present test, it was found that when the force F was removed, the squashed tubular body 110C returned to the original shape (the shape of the tubular body 110A), and therefore it was found that the deformation of the tubular body 110A was elastic deformation. Therefore, the present test was a different test from the evaluation test of the kinking (meaning that the tubular body is plastically deformed and does not return to the original shape).

TABLE 3

Roundness rate

|  | Example 1 (t1 = 0.10) | Example 2 (t1 = 0.12) | Comparative Example 1 (t1 = 0.12) | Comparative Example 2 (t1 = 0.10) | Comparative Example 3 (t1 = 0.12) |
| --- | --- | --- | --- | --- | --- |
| Test 1 | 0.75 | 0.95 | 0.61 | 0.57 | 0.74 |
| Test 2 | 0.70 | 0.95 | 0.64 | 0.52 | 0.70 |
| Test 3 | 0.72 | 0.92 | 0.62 | 0.51 | 0.73 |
| Test 4 | 0.71 | 0.88 | 0.62 | 0.51 | 0.68 |
| Test 5 | 0.71 | 0.94 | 0.60 | 0.56 | 0.67 |
| Average value | 0.72 | 0.93 | 0.62 | 0.53 | 0.70 |
| Maximum value | 0.75 | 0.95 | 0.64 | 0.57 | 0.74 |
| Minimum value | 0.70 | 0.88 | 0.60 | 0.51 | 0.67 |

TABLE 4

Lumen retention rate (roundness rate/wall thickness)

|  | Example 1 (t1 = 0.10) | Example 2 (t1 = 0.12) | Comparative Example 1 (t1 = 0.12) | Comparative Example 2 (t1 = 0.10) | Comparative Example 3 (t1 = 0.12) |
| --- | --- | --- | --- | --- | --- |
| Test 1 | 7.5 | 7.9 | 5.1 | 5.7 | 6.2 |
| Test 2 | 7.0 | 7.9 | 5.3 | 5.2 | 5.8 |
| Test 3 | 7.2 | 7.7 | 5.2 | 5.1 | 6.1 |
| Test 4 | 7.1 | 7.3 | 5.2 | 5.1 | 5.7 |
| Test 5 | 7.1 | 7.8 | 5.2 | 5.6 | 5.6 |
| Average value | 7.2 | 7.7 | 5.1 | 5.3 | 5.9 |
| Maximum value | 7.5 | 7.3 | 5.3 | 5.7 | 6.2 |
| Minimum value | 7.0 | 7.9 | 5.1 | 5.1 | 5.6 |

As can be seen from Table 3, when comparing Example 2 in which the wall thickness was formed to be 0.12 mm and Comparative Example 1 and Comparative Example 3 in which the wall thickness was formed to be 0.12 mm, the roundness rate was large in Example 2, that is, the deformation of the tubular body 110A when the force F was applied from the axially orthogonal direction could be suppressed. Based on the results, it was found that in the case in which a microcrystalline polyamide resin obtained by polymerizing dodecanedioic acid and 4,4'-methylenebis (cyclohexylamine) was used as the material forming the tubular body 110A, the deformation of the tubular body 110A when the force F was applied from the axially orthogonal direction could be suppressed, compared to the case in which the ethylene tetrafluoroethylene resin and the polyamide 12 resin were used.

In addition, generally, as the wall thickness becomes thicker, the deformation of the tubular body 110A could be suppressed by resisting the force F from the axially orthogonal direction, and thus the roundness rate becomes larger, that is, the roundness rate depends on the wall thickness t1 of the tubular body 110A. Therefore, in addition to the roundness rate, the lumen retention rate (roundness rate/wall thickness t1) considering the dependency of the roundness rate on the wall thickness t1 was evaluated. As can be seen from Table 4, a minimum value 7.0 of the lumen retention rate of Examples 1 and 2 is larger than a maximum value 6.2 of the lumen retention rate of Comparative Examples 1 to 3, that is, the tubular bodies 110A of Examples 1 and 2 have lumen retention rates larger than those of lumen retention rates of Comparative Examples 1 to 3. Based on the results, it was found that in the case in which the resin obtained by polymerizing dodecanedioic acid and 4,4'-methylenebis(cyclohexylamine) was used as the material forming the tubular body 110A, the lumen retention rate was large and the deformation of the tubular body 110A when the force F was applied from the axially orthogonal direction could be suppressed, compared to the case in which the ethylene tetrafluoroethylene resin and the polyamide 12 resin were used.

As described above, the introducer sheath 100 according to the exemplary embodiment of the disclosure includes the tubular body 110 that is percutaneously inserted into a body lumen, and the hub 120 that is connected to the proximal portion of the tubular body 110. The tubular body 110 contains the polyamide resin having a structural unit derived from a cyclic aliphatic hydrocarbon, and the wall thickness/inner diameter of the tubular body is 1/14 or less, and the kink radius/outer diameter of the tubular body is less than 10.

In the tubular body 110 according to the exemplary embodiment, the wall thickness/inner diameter ratio is smaller than that of the tubular body in the related art. Therefore, it is possible that the tubular body 110 has a large inner diameter and thin wall thickness. In addition, the tubular body 110 contains a polyamide resin having a structural unit derived from a cyclic aliphatic hydrocarbon and has a small ratio of the kink radius/outer diameter. For this reason, the kink resistance of the tubular body 110 can be enhanced. Accordingly, it is possible to provide the introducer sheath 100 including the tubular body 110 formed such that the inner diameter is larger, the wall thickness is thinner, and the kink resistance is enhanced compared to those of the tubular body in the related art.

In addition, the tubular body 110 has the tapered tubular distal portion 111, and the tubular main body portion 115 that is disposed on the proximal side of the tubular distal portion 111. In the tubular body 110, the wall thickness/inner diameter of the tubular main body portion 115 is 1/14 or less, and the kink radius/outer diameter of the tubular main body portion 115 is 10 or less. Therefore, it is possible to enhance the insertion properties of the tubular distal portion 111 into a body lumen, and it is possible to enhance the kink resistance of the tubular main body portion 115 while the wall thickness of the tubular main body portion 115, into which various medical instruments are inserted, is made thin.

In addition, in the tubular body 110, because the tubular distal portion 111 is configured to be more rigid than the tubular main body portion 115, turnover is prevented from occurring in the tubular distal portion 111 when the tubular body 110 is inserted into a body lumen, and the kink resistance of the tubular distal portion 111 is enhanced.

In addition, the introducer sheath 100 includes the strain relief portion 130 that covers the interlock portion 125*a* of the tubular body 110 and the hub 120. In the tubular body 110, the kink generation angle occurring, when a position 3 cm away from the distal end of the hub 120 is pressed, is 32° or greater, in a state where the proximal end of the tubular body 110 is fixed to the lumen 126 of the hub 120, and the strain relief portion 130 is provided. The strain relief portion 130 protects the interlock portion 125*a* of the tubular body 110 and the hub 120 from the outside and adjusts a change in rigidity in the distal end P1 of the hub 120. In the introducer sheath 100, since the kink generation angle of the tubular body 110 is 32° or greater, in a state where the strain relief portion 130 is disposed, the kink resistance of the tubular body 110 is enhanced in a state where the introducer sheath 100 is held and fixed at the proximal side of the introducer sheath 100.

In addition, when the solid rod member 600 with an outer diameter of 2 mm is pushed against the tubular body 110 with the force F of 150 gf in a direction perpendicular to the tubular body 110, the lumen retention rate of the position where the rod member 600 is pushed against the tubular body 110 is 6.3 or greater, the lumen retention rate being defined as a roundness rate of the inner surface/wall thickness t1 of the tubular body 110. Therefore, the tubular body 110 can be suppressed from being squashed in the radial direction when the tubular body 110 is applied with the force for tightening the tubular body in the radial direction from biological tissues around the puncture site. As a result, the operator can smoothly introduce a medical instrument into the hollow portion 116.

The polyamide resin having a structural unit derived from a cyclic aliphatic hydrocarbon has the structural unit (A) derived from a linear aliphatic dicarboxylic acid and the structural unit (B) derived from an alicyclic diamine. Therefore, it is possible to provide the introducer sheath 100 including the tubular body 110 formed such that the inner diameter is larger, the wall thickness is thinner, and the kink resistance is enhanced compared to those of the tubular body in the related art.

In addition, the introducer 10 of the exemplary embodiment includes the introducer sheath 100 and the dilator 200 that has the dilator main body 210 insertable into the hollow portion 116 of the tubular body 110. The dilator main body 210 has flexural rigidity higher than that of the tubular body 110. Therefore, when the tubular body 110 is inserted into a body lumen in a state where the dilator main body 210 is inserted into the hollow portion 116 of the tubular body 110, a strong elastic force is applied to the tubular body 110 due to the dilator main body 210, and therefore turnover and kinking can be prevented from occurring in the tubular body 110.

Hereinbefore, the introducer sheath was explained with reference to the exemplary embodiment, but the disclosure herein is not limited to only each configuration described in the disclosure here and may be modified as appropriate based on the description of the claims.

For example, in the explanation of the exemplary embodiment, the tubular body has the tapered tubular distal portion, but the tubular body may not have the tapered tubular distal portion. In the case where the tubular body does not have the tapered tubular distal portion, in the tubular body, the wall thickness/inner diameter is 1/14 or less and the kink radius/outer diameter is 10 or less over the entire length in the axis direction.

Furthermore, for example, the specific structure of the introducer sheath and the specific structure of the dilator are not limited to those described with reference to the drawings and may be modified as appropriate as long as the introducer sheath and the dilator can function as the introducer.

In addition, specific configurations of the introducer sheath according to the exemplary embodiment of the disclosure are not limited as long as the introducer sheath includes the hub, and the tubular body contains the polyamide resin having the structural unit derived from a cyclic aliphatic hydrocarbon, in which the wall thickness/inner diameter of the tubular body is 1/14 or less and the kink radius/outer diameter of the tubular body is 10 or less. Therefore, the dimensions and the physical properties, materials, and the like of the members described in the disclosure herein may be modified as appropriate.

What is claimed is:

1. An introducer sheath comprising:
    a tubular body configured to be percutaneously inserted into a body lumen; and
    a hub connected to a proximal portion of the tubular body;
    the tubular body comprising a polyamide resin having a structural unit (A) derived from a linear aliphatic dicarboxylic acid and a structural unit (B) derived from an alicyclic diamine, wherein the structural unit (B) is 1 mol % to 49 mol % with respect to a total 100 mol % of the structural unit (A) and the structural unit (B); and
    wherein a ratio of a wall thickness to an inner diameter of the tubular body is 1/14 or less, and a ratio of a kink radius to an outer diameter of the tubular body is 10 or less.

2. The introducer sheath according to claim 1,
    wherein the tubular body includes a tapered tubular distal portion, and a tubular main body portion disposed on a proximal side of the tubular distal portion; and
    wherein, in the tubular body, a wall thickness/inner diameter ratio of the tubular main body portion is 1/14 or less, and a kink radius/outer diameter ratio of the tubular main body portion is 10 or less.

3. The introducer sheath according to claim 2,
    wherein, in the tubular body, the tubular distal portion is configured to be more rigid than the tubular main body portion.

4. The introducer sheath according to claim 2, wherein, in the tubular body, the tapered tubular distal portion has a tapered shape in which an inner diameter is constant and an outer diameter tapers toward a distal side of the tubular body.

5. The introducer sheath according to claim 1, further comprising:
    a strain relief portion configured to cover an interlock portion of the tubular body and the hub;
    wherein, in the tubular body, a kink generation angle occurring, when a position 3 cm away from a distal end of the hub is pressed, is 32° or greater, in a state where a proximal end of the tubular body is fixed to a lumen of the hub, and the strain relief portion is covering the interlock portion of the tubular body and the hub.

6. The introducer sheath according to claim 5, wherein the strain relief portion includes a concave portion at a position overlapping a distal end of the hub.

7. The introducer sheath according to claim 1,
wherein, when a solid rod member with an outer diameter of 2 mm is pushed against the tubular body with a force of 150 gf in a direction perpendicular to the tubular body, a lumen retention rate of a position where the solid rod member is pushed against the tubular body is 6.3 or greater, the lumen retention rate being defined as a roundness rate of an inner surface of the tubular body/the wall thickness of the tubular body.

8. The introducer sheath according to claim 1, wherein the ratio of the wall thickness to the inner diameter of the tubular body is 1/22.2 to 1/14.8.

9. The introducer sheath according to claim 1, wherein the ratio of the kink radius to the outer diameter of the tubular body is 8.3 or less.

10. An introducer comprising:
an introducer sheath comprising a tubular body configured to be percutaneously inserted into a body lumen, a hub connected to a proximal portion of the tubular body, the tubular body including a polyamide resin having a structural unit (A) derived from a linear aliphatic dicarboxylic acid and a structural unit (B) derived from an alicyclic diamine, wherein the structural unit (B) is 1 mol % to 49 mol % with respect to a total 100 mol % of the structural unit (A) and the structural unit (B), and wherein a ratio of a wall thickness to an inner diameter of the tubular body is 1/14 or less, and a ratio of a kink radius to an outer diameter of the tubular body is 10 or less;
a dilator including a dilator main body insertable into a lumen of the tubular body; and
wherein the dilator main body has higher flexural rigidity than that of the tubular body.

11. The introducer according to claim 10, wherein a wall thickness of the dilator main body is thicker than the wall thickness of the tubular body.

12. The introducer according to claim 10, wherein the dilator main body is made of a material having a bending modulus of elasticity higher than that of a material of the tubular body.

13. The introducer according to claim 10,
wherein the tubular body includes a tapered tubular distal portion, and a tubular main body portion disposed on a proximal side of the tubular distal portion; and
wherein, in the tubular body, a wall thickness/inner diameter ratio of the tubular main body portion is 1/14 or less, and a kink radius/outer diameter ratio of the tubular main body portion is 10 or less.

14. The introducer according to claim 13, wherein, in the tubular body, the tapered tubular distal portion has a tapered shape in which an inner diameter is constant and an outer diameter tapers toward a distal side of the tubular body.

15. The introducer according to claim 10, further comprising:
a strain relief portion configured to cover an interlock portion of the tubular body and the hub;
wherein, in the tubular body, a kink generation angle occurring, when a position 3 cm away from a distal end of the hub is pressed, is 32° or greater, in a state where a proximal end of the tubular body is fixed to a lumen of the hub, and the strain relief portion is covering the interlock portion of the tubular body and the hub.

16. The introducer according to claim 15, wherein the strain relief portion includes a concave portion at a position overlapping a distal end of the hub.

17. The introducer according to claim 10, wherein the ratio of the wall thickness to the inner diameter of the tubular body is 1/22.2 to 1/14.8.

18. The introducer according to claim 10, wherein the ratio of the kink radius to the outer diameter of the tubular body is 8.3 or less.

19. An introducer sheath comprising:
a tubular body configured to be percutaneously inserted into a body lumen, the tubular body comprising a polyamide resin having a structural unit (A) derived from a linear aliphatic dicarboxylic acid and a structural unit (B) derived from an alicyclic diamine;
a hub connected to a proximal portion of the tubular body;
a ratio of a wall thickness to an inner diameter of the tubular body is 1/14 or less, and a ratio of a kink radius to an outer diameter of the tubular body is 10 or less; and
wherein, when a solid rod member with an outer diameter of 2 mm is pushed against the tubular body with a force of 150 gf in a direction perpendicular to the tubular body, a lumen retention rate of a position where the solid rod member is pushed against the tubular body is 6.3 or greater, the lumen retention rate being defined as a roundness rate of an inner surface of the tubular body/the wall thickness of the tubular body.

\* \* \* \* \*